United States Patent

Afzali-Ardakani et al.

(10) Patent No.: US 10,209,186 B2
(45) Date of Patent: Feb. 19, 2019

(54) CHEMICAL SENSING BASED ON PLASMON RESONANCE IN CARBON NANOTUBES

(71) Applicant: INTERNATIONAL BUSINESS MACHINES CORPORATION, Armonk, NY (US)

(72) Inventors: Ali Afzali-Ardakani, Ossining, NY (US); Abram L. Falk, New Britain, CT (US); Damon B. Farmer, Eastchester, NY (US); Shu-Jen Han, Cortlandt Manor, NY (US); George S. Tulevski, Croton-on-Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 25 days.

(21) Appl. No.: 15/396,902

(22) Filed: Jan. 3, 2017

(65) Prior Publication Data

US 2018/0188171 A1  Jul. 5, 2018

(51) Int. Cl.
*G01N 21/55* (2014.01)
*G01N 21/552* (2014.01)

(52) U.S. Cl.
CPC ................. *G01N 21/554* (2013.01)

(58) Field of Classification Search
CPC ...... A61B 5/0075; G01N 21/65; G01N 21/00; G01N 21/66; G01N 21/648; G01N 21/554; G01N 21/553; G01N 2021/3595; G01B 9/02044; G01J 3/44; G02F 2203/10
USPC .... 356/301, 432–440, 445–448; 250/339.11, 250/339.12
See application file for complete search history.

(56) References Cited

U.S. PATENT DOCUMENTS

| | | | |
|---|---|---|---|
| 6,778,316 B2 | 8/2004 | Halas et al. | |
| 7,450,227 B2 | 11/2008 | Dwight et al. | |
| 7,456,972 B2 * | 11/2008 | Ke | B82Y 15/00 356/445 |
| 7,671,995 B2 | 3/2010 | Lin et al. | |
| 7,738,096 B2 | 6/2010 | Zhao et al. | |
| 8,009,284 B2 * | 8/2011 | Xiao | G01J 5/02 250/370.01 |
| 8,383,416 B2 | 2/2013 | Poponin | |

(Continued)

FOREIGN PATENT DOCUMENTS

CN   104777152   7/2015

OTHER PUBLICATIONS

J. Sebastian Gómez-Diaz, et al., Graphene-Based Hyperbolic Metasurfaces, 2016 10th European Conference on Antennas and Propagation (EuCAP), Davos, Apr. 2016, pp. 1-4.

(Continued)

*Primary Examiner* — Hoa Pham
(74) *Attorney, Agent, or Firm* — Tutunjian & Bitetto, P.C.; Vazken Alexanian

(57) ABSTRACT

A chemical sensor, methods of forming the same, and methods of performing chemical detection include a carbon nanotube test surface. A detector is configured to receive a signal from the carbon nanotube test surface responsive to illumination on the nanotube test surface. A matching module is configured to determine whether a chemical is present at the carbon nanotube test surface based on a comparison between the signal and a spectral profile of the chemical.

17 Claims, 8 Drawing Sheets

(56) References Cited

U.S. PATENT DOCUMENTS

| | | | |
|---|---|---|---|
| 8,506,887 B2* | 8/2013 | Rong | G01N 21/552 |
| | | | 356/446 |
| 8,535,109 B1* | 9/2013 | Wei | H01J 9/025 |
| | | | 313/311 |
| 8,765,488 B2 | 7/2014 | Strano et al. | |
| 9,410,934 B2 | 8/2016 | Robinson et al. | |
| 9,512,545 B2* | 12/2016 | Zhang | B82Y 10/00 |
| 2011/0063613 A1* | 3/2011 | Sun | G01N 21/65 |
| | | | 356/301 |
| 2012/0062880 A1* | 3/2012 | Sun | G01N 21/65 |
| | | | 356/301 |
| 2012/0086021 A1* | 4/2012 | Wang | G01N 21/658 |
| | | | 257/84 |
| 2012/0125084 A1* | 5/2012 | Robinson | C23C 16/0272 |
| | | | 73/31.05 |
| 2014/0356411 A1 | 12/2014 | Fan et al. | |
| 2016/0033401 A1 | 2/2016 | Farmer | |

OTHER PUBLICATIONS

Katrin Kneipp et al., Single Molecule Detection Using Surface-Enhanced Raman Scattering (SERS), The American Physical Society, Mar. 3, 1997, vol. 78, No. 9, pp. 1667-1670.

* cited by examiner

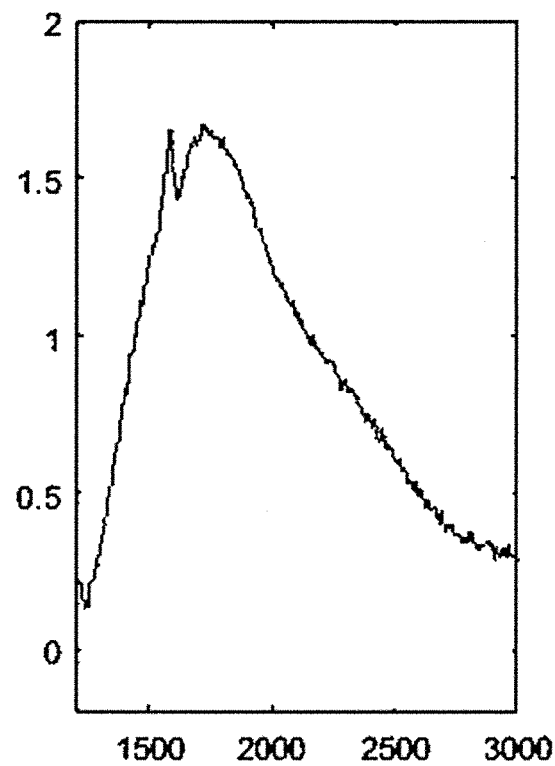
FIG. 2
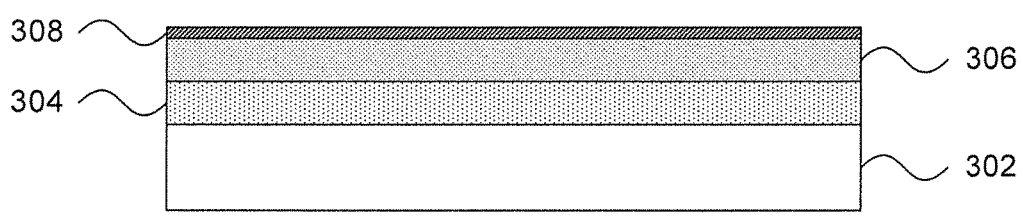
FIG. 3
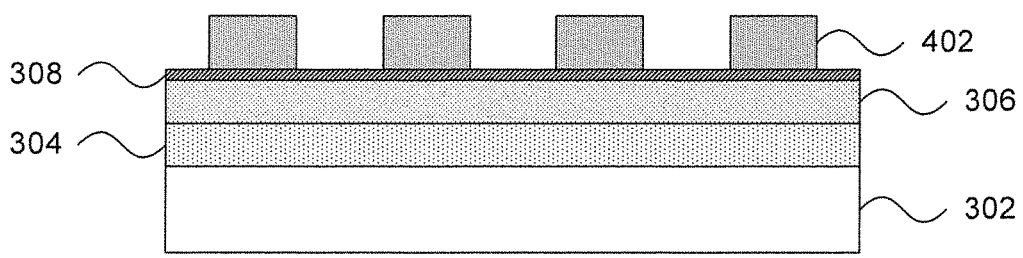

CHEMICAL SENSING BASED ON PLASMON RESONANCE IN CARBON NANOTUBES

BACKGROUND

Technical Field

The present invention generally relates to chemical sensors and, more particularly, to chemical sensors that use plasmonic resonance in nanotube structures.

Description of the Related Art

Surface plasmon resonance describes oscillations in electric charges at the surface of a material that are coupled with an electromagnetic field. For example, surface plasmons may be used to represent electron oscillations at the interface between a metal and air. Surface plasmon resonance can be stimulated by illuminating the surface with light of an appropriate frequency, where the frequency of the light matches the natural frequency of the surface plasmons.

Surface plasmon resonance is used for molecular detection probes. For example, in surface-enhanced Raman scattering, plasmonic effects enhance the Raman signal from molecules by up to a factor of $10^{10}$, enabling single-molecule detection. Surface plasmon resonance-based immunoassays also allow for label-free detection of analytes. Such sensors are available for a wide variety of applications, ranging from gas sensing and explosive detection to cancer detection and glucose sensing.

However, conventional sensors based on surface plasmon resonance have two significant drawbacks. First, in the portion of the spectrum from visible light to the near infrared, such sensors have imperfect chemical sensitivity due to many molecules being optically active in that region. Second, it can be difficult to miniaturize bulk plasmonic materials. For example, commonly used plasmonic metals, such as silver, will oxidize near their surface.

SUMMARY

A chemical sensor includes a carbon nanotube test surface. A detector is configured to receive a signal from the carbon nanotube test surface responsive to illumination on the nanotube test surface. A matching module is configured to determine whether a chemical is present at the carbon nanotube test surface based on a comparison between the signal and a spectral profile of the chemical.

A method of chemical sensing includes illuminating a carbon nanotube test surface. A signal is detected from the carbon nanotube test surface responsive to the illumination of the carbon nanotube test surface. It is determined whether the chemical is present at the carbon nanotube test surface based on a comparison between the signal and a spectral profile of the chemical.

A method of forming a chemical sensor includes forming a dielectric layer on an electrode. A carbon nanotube film is deposited on the dielectric layer. The carbon nanotube film is patterned into multiple strips.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 2 is a reflected spectral response from a chemical sensor in accordance with the present embodiments;

FIG. 3 is a cross-sectional view of a step in the fabrication of a chemical sensor in accordance with the present embodiments;

DETAILED DESCRIPTION

Embodiments of the present invention provide surface plasmon resonance sensors that use carbon nanotubes to provide a surface interface. Carbon nanotubes provide resonances in the spectral range from mid-infrared to terahertz; can be tuned by chemical doping, electrostatic gating, or by tuning their length; provide a high degree of optical confinement; provide molecular specificity without surface functionalization; and can be electrically integrated into photothermoelectric chemical sensors.

Figure 1:
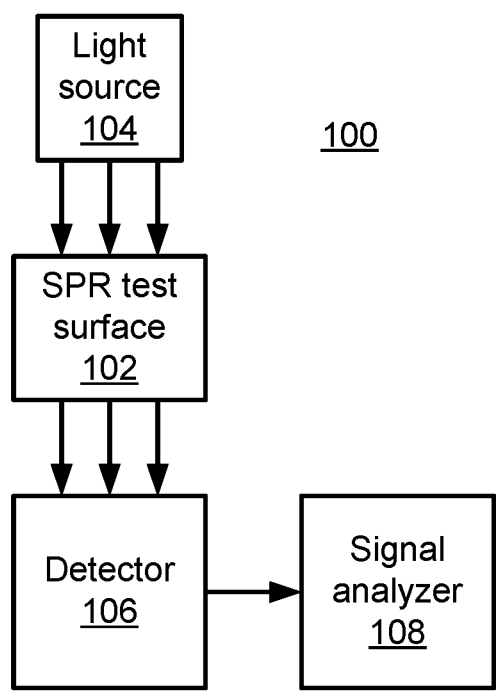
FIG. 1 is a block diagram of a chemical sensor in accordance with the present embodiments.

Referring now to FIG. 1, a sensor system 100 is shown. A surface plasmon resonance test surface 102 is illuminated by a light source 104. Reflected light is collected at a detector 106 and analyzed by signal analyzer 108. It is specifically contemplated that the light source may be a broadband source such as, e.g., an incandescent bulb, but it should be understood that other light sources, such as light emitting diodes, lasers, and fluorescents, may be used instead.

The surface plasmon resonance test surface 102 of the present embodiments uses a low-dimensional material. Although it is specifically contemplated that carbon nanotubes may be used, it should be understood that other low-dimensional materials (i.e., materials that exhibit one- or two-dimensional plasmon resonances) may be used instead. In addition, materials other than carbon may be used, including for example inorganic nanotube materials.

The plasmonic resonances of low-dimensional materials, such as graphene and carbon nanotubes, have low resonance frequencies relative to conventional bulk materials. These resonance frequencies, which can be tuned by doping and/or patterning, overlap the vibration energies of molecules and biomolecules. When the vibrational and plasmon modes overlap, the absorption from the vibrational mode will be plasmonically enhanced. The presence of molecules of interest can then be sensitively detected by analyzing changes in surface plasmon resonance absorption. In the far infrared and terahertz regimes, the vibrational modes of molecules can form a unique fingerprint, with a one-to-one correspondence between the vibrational spectrum and a specific module. This fingerprint allows the nanotube-based sensor to be chemically specific.

The surface plasmon resonance test surface 102 is therefore exposed to a substance or environment under test. When a molecule of interest interacts with the test surface 102, the reflected light absorbed by the detector 106 changes according to the fingerprint, and the signal analyzer 108 detects the signature. The analysis performed by the signal analyzer 108 may include, for example, Fourier transform infrared spectroscopy.

The low-dimensional geometry of graphene and carbon nanotubes also confines the plasmonic modes better than bulk materials. When a plasmonic structure is miniaturized, additional spatial confinement of the plasmonic mode can be achieved and, in turn, a higher Purcell enhancement factor P can be provided, which characterizes the plasmonic enhancement to fluorescence. For example, the Purcell enhancement of a molecule coupled to an ideal plasmonic cylinder having a radius R will scale as ~1/R. Miniaturizing the plasmonic materials furthermore makes the materials closer to the size scale of the molecules to be detected, opening up opportunities for surface plasmon resonance labels to be attached to functional molecules.

The use of carbon nanotubes in particular provides the ability to functionalize the nanotubes in solution, such that they will preferentially bind to certain analytes. In addition, semiconducting nanotubes have a higher photothermoelectric coefficient than does, e.g., graphene, providing electrically integrated plasmonic sensors that have superior sensitivity.

Referring now to FIG. 2, an exemplary spectral curve is shown for detection using a carbon nanotube surface plasmon resonance test surface 102. The vertical axis shows a magnitude of absorption of light (i.e., a decrease in light that is detected at the detector 106 compared to a baseline) measured as a percentage. The horizontal axis shows the wavenumber of the light in inverse centimeters—wavenumber essentially being a measurement of the number of wave cycles present per unit length. A relatively broad peak is centered around 1,800/cm and has a width of roughly 700/cm. This broad peak represents the plasmonic resonance of the nanotubes. There is a sharp peak within the broad peak that is centered at about 1600/cm, which indicates a vibrational C-C mode. The C-C mode is the E1u infrared-active mode of a nanotube.

Referring now to FIG. 3, a cross-sectional view of a step in the fabrication of a surface plasmon resonance test surface 102 is shown. A gate electrode 304 is formed on a semiconductor substrate 302. A dielectric layer 306 is formed over the gate electrode 304 and may be formed from any appropriate insulating material such as, e.g., silicon dioxide. In one specific embodiment, the dielectric layer 306 is formed with about 10 nm of silicon dioxide and between about 0 nm and about 40 nm of diamond-like carbon on top. The diamond-like carbon provides a non-polar spacer that controls the coupling between plasmons in the nanotubes and polar photons in the silicon dioxide. A carbon nanotube film 308 is then formed on the dielectric layer 306.

The gate electrode 304 is used to tune the resonance of the final device. In particular, applying a voltage to the gate electrode 304 electrostatically modifies the charge density in the nanotubes. In turn, this charge density affects the plasmon resonance frequency and, thus, also affects the frequency of light that is absorbed when a chemical to be detected is present.

The semiconductor substrate 302 may be a bulk-semiconductor substrate. In one example, the bulk-semiconductor substrate may be a silicon-containing material. Illustrative examples of silicon-containing materials suitable for the bulk-semiconductor substrate include, but are not limited to, silicon, silicon germanium, silicon germanium carbide, silicon carbide, polysilicon, epitaxial silicon, amorphous silicon, and multi-layers thereof. Although silicon is the predominantly used semiconductor material in wafer fabrication, alternative semiconductor materials can be employed, such as, but not limited to, germanium, gallium arsenide, gallium nitride, cadmium telluride and zinc selenide. Although not depicted herein, the semiconductor substrate 302 may also be a semiconductor on insulator (SOI) substrate, for example with a buried oxide layer underling a semiconductor layer.

The carbon nanotube layer 308 may be deposited using, e.g., the Langmuir-Schaefer process, although any other appropriate growth or deposition process may be used instead to produce a uniform, densely distributed film of carbon nanotubes. This process creates a film of nanotubes that may be between about 2 and about 10 monolayers thick. It is specifically contemplated that the carbon nanotube layer 308 may have a thickness of about 6 nm and may be formed from about 99.9% semiconducting nanotubes. It should be noted that the carbon nanotubes being aligned and roughly parallel with another increases the sharpness of the resonance signal, and improves the sensitivity of the sensor, but some embodiments may include non-aligned nanotubes.

Figure 4:
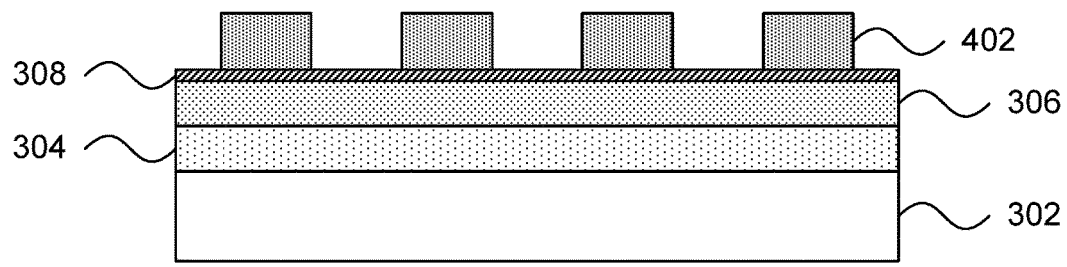
FIG. 4 is a cross-sectional view of a step in the fabrication of a chemical sensor in accordance with the present embodiments.

Referring now to FIG. 4, a cross-sectional view of a step in the fabrication of a surface plasmon resonance test surface 102 is shown. A mask 402 is formed by depositing a layer of, e.g., poly methyl methacrylate (PMMA) onto the nanotube layer 308. The mask 402 may be formed by, e.g., spinning the PMMA onto the surface and allowing the material to solidify, followed by etching a pattern into the PMMA material. Electron-beam lithography may be used to pattern stripes into the PMMA material, but it should be understood that any appropriate anisotropic etch process may be used instead so long as it does not damage the underlying nanotube layer 308. While a striped pattern is specifically contemplated for the mask 402, it should be understood that any other appropriate pattern, for example including non-linear patterns and linear patterns having varying thicknesses may, be used instead.

In one specific embodiment, the mask 402 leaves gaps having a width of between about 50 nm and about 500 nm. These gaps are oriented transverse to an orientation of the nanotubes in the nanotube layer 308, such that the nanotubes in the nanotube layer 308 have lengths roughly the same as the widths of the gaps.

Figure 5:
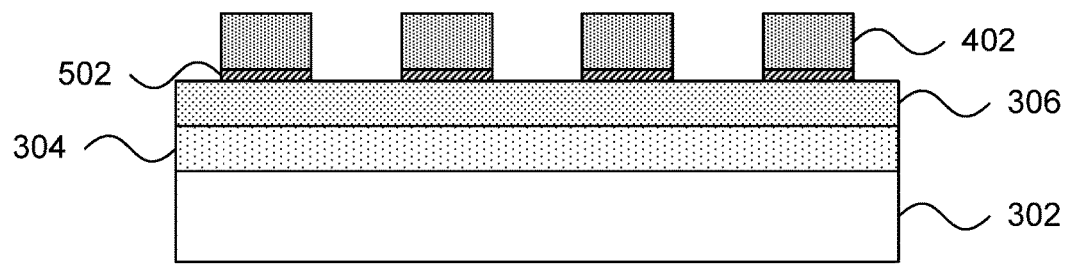
FIG. 5 is a cross-sectional view of a step in the fabrication of a chemical sensor in accordance with the present embodiments.

Referring now to FIG. 5, a cross-sectional view of a step in the fabrication of a surface plasmon resonance test surface 102 is shown. The exposed portions of the nanotube layer 302 are etched away, leaving only nanotube strips 502 protected underneath the mask 402. The etch may be performed using an $O_2$-based reactive ion etch (RIE) or any other appropriate anisotropic etch.

RIE is a form of plasma etching in which during etching the surface to be etched is placed on a radio-frequency powered electrode. Moreover, during RIE the surface to be etched takes on a potential that accelerates the etching species extracted from plasma toward the surface, in which the chemical etching reaction is taking place in the direction normal to the surface. Other examples of anisotropic etching that can be used at this point of the present invention include ion beam etching, plasma etching or laser ablation.

Figure 6:
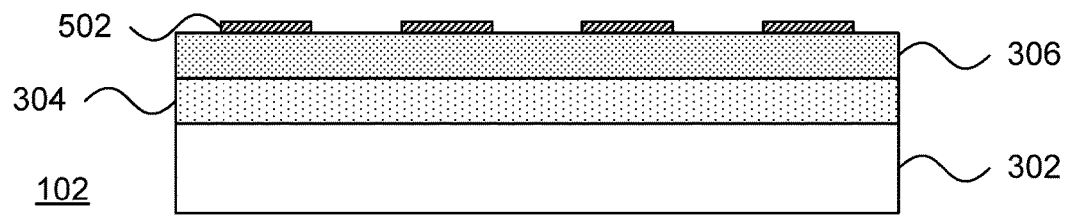
FIG. 6 is a cross-sectional view of a step in the fabrication of a chemical sensor in accordance with the present embodiments.

Referring now to FIG. 6, a cross-sectional view of a step in the fabrication of a surface plasmon resonance test surface 102 is shown. The mask 402 is removed using any appropriate selective etch, for example a wet or dry chemical etch such as acetone, that selectively removes the mask material without harming the underling nanotube strips 502. In addition, the nanotube strips 502 may be doped. In one specific embodiment, the nanotube strips 502 are doped to p-type via exposure to $NO_2$ gas at, e.g., 25° C. under a pressure of about 300 mTorr for about 5 minutes, although it should be understood that other forms of doping may be used instead. Doping the nanotube strips 502 provides tuning in the frequency tuning of the sensor. At this stage, electrical connections may be formed to the gate electrode layer 304 in any appropriate manner and the finished device may be exposed to a chemical or environment to sense particular chemicals.

Figure 7:
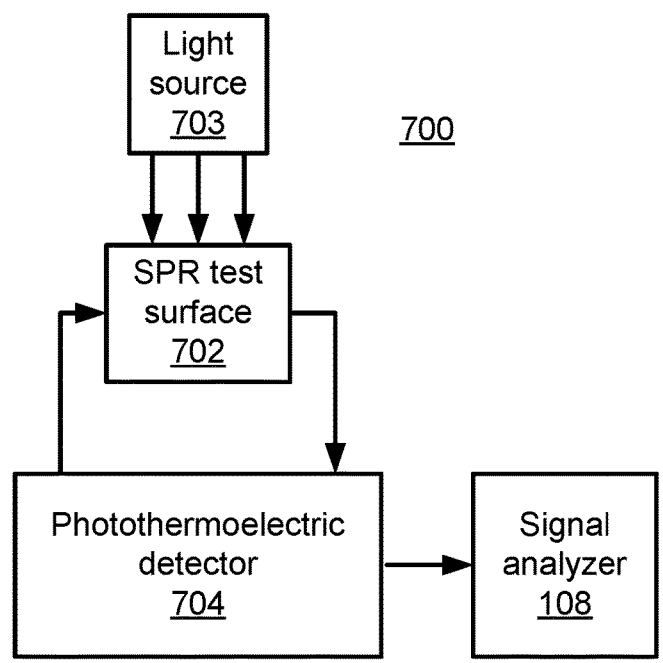
FIG. 7 is a block diagram of an alternative embodiment of a chemical sensor in accordance with the present embodiments.

Referring now to FIG. 7, an alternative embodiment of a sensor system 700 is shown. In this embodiment, the surface plasmon resonance test surface 702 has conductive terminals at the ends of its nanotube strips. A photothermoelectric detector 704 measures photothermoelectric currents generated in the nanotube strips when illuminated by a narrowband light source 703, with an output frequency tuned to the molecular vibration of interest. The photothermoelectric currents represent the spectral resonance response of the test surface 702 and are provided to the signal analyzer 108 for analysis and comparison to one or more chemical spectrum fingerprints.

In this embodiment, narrowband light source 703 is tuned to the expected vibrational resonance of the chemical being detected. Because detection is performed using the photothermoelectric current, no spectral analysis is performed. The degree of absorption, and hence the magnitude of the current, is modulated by the presence and quantity of the chemical to be detected.

Figure 8:
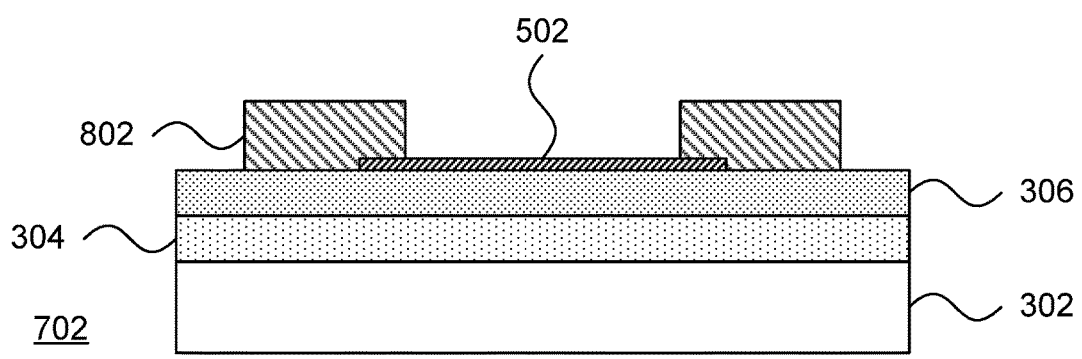
FIG. 8 is a cross-sectional view of a step in the fabrication of an alternative embodiment of a chemical sensor in accordance with the present embodiments.

Referring now to FIG. 8, additional detail on the surface plasmon resonance test surface 702 is shown. In this embodiment, conductive contacts 802 are formed at the ends of the nanotube strips 502. It is specifically contemplated that the conductive contacts 802 may be metal or metallic electrodes, for example formed from any appropriate material such as tungsten, nickel, titanium, molybdenum, tantalum, copper, platinum, silver, gold, ruthenium, iridium, rhenium, rhodium, silicides, germanicides, or any other appropriately conductive material or mixture of materials.

The conductive contacts form electrical connections to the photothermoelectric detector 704. When light from the narrowband light source 703 strikes the surface plasmon resonance test circuit 702 in the presence of the chemical in question, the nanotube strips 502 absorb the light and drive a photothermoelectric current between the conductive contacts 802, thereby providing the detection signal. When the molecule in question is present, the absorption spectrum of the nanotube strips 502 is modified, resulting in a modification of the photothermoelectric signal.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B)

only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein s for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative teens are intended to encompass different orientations of the device in use or operation addition to the orientation depicted in the FIGS. For example, if the device in the FIGS. is turned over, elements described as "below" or "beneath" other elements or features would then be oriented "above" the other elements or features. Thus, the term. "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers car also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Figure 9:
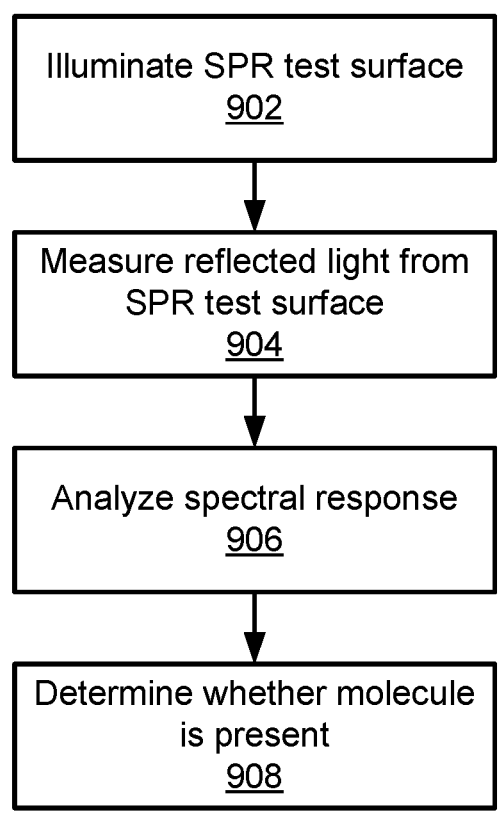
FIG. 9 is a block/flow diagram of a method of chemical detection in accordance with the present embodiments.

Referring now to FIG. 9, a method of molecular detection is shown. Block 902 illuminates a surface plasmon resonance test surface 102 with broadband input light from, e.g., a light source 104. Block 904 measures the light reflected from the test surface 102, which provides a spectral response based on the absorption characteristics of the nanotube strips 502 in the test surface 102. Block 906 analyzes the spectral response to determine whether the spectral response matches a spectral fingerprint of one or more molecules. If block 906 finds a match, block 908 determines that the corresponding molecule is present at the test surface 102.

Figure 10:
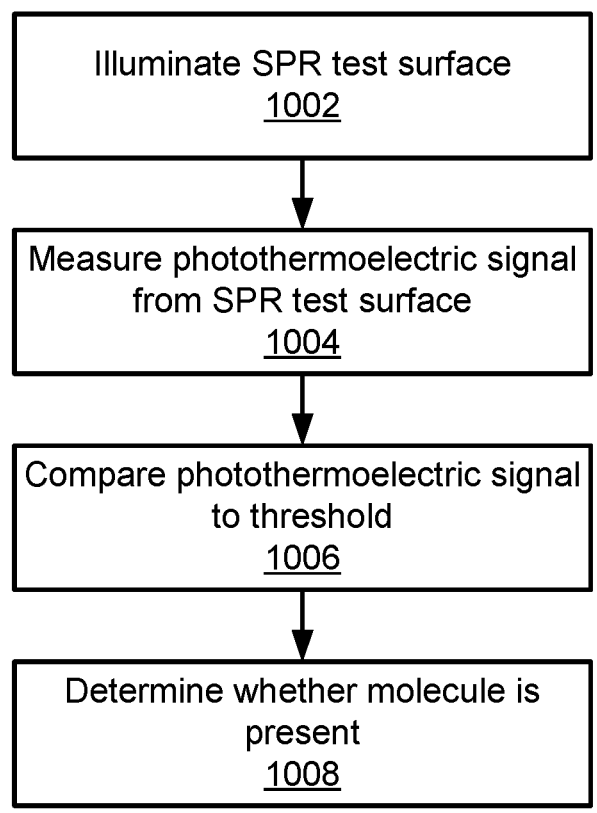
FIG. 10 is a block/flow diagram of a method of chemical detection in accordance with the present embodiments.

Referring now to FIG. 10, an alternative method of molecular detection is shown. Block 1002 illuminates a surface plasmon resonance test surface 702 with narrowband light from, e.g., a light source 703. Block 1004 measures a photothermoelectric signal generated by the test surface 702, which provides a spectral response based on the absorption characteristics of the nanotube strips 502 in the test surface 702. Block 1006 compares the photothermoelectric signal to the threshold. If the photothermoelectric signal is greater than a threshold, block 1008 indicates that the corresponding molecule is present at the test surface 702. If not, block 1008 indicates that the molecule is not present. In some embodiments, block 1008 may indicate an amount of the molecule that is present based on the magnitude of the photothermoelectric signal.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 11:
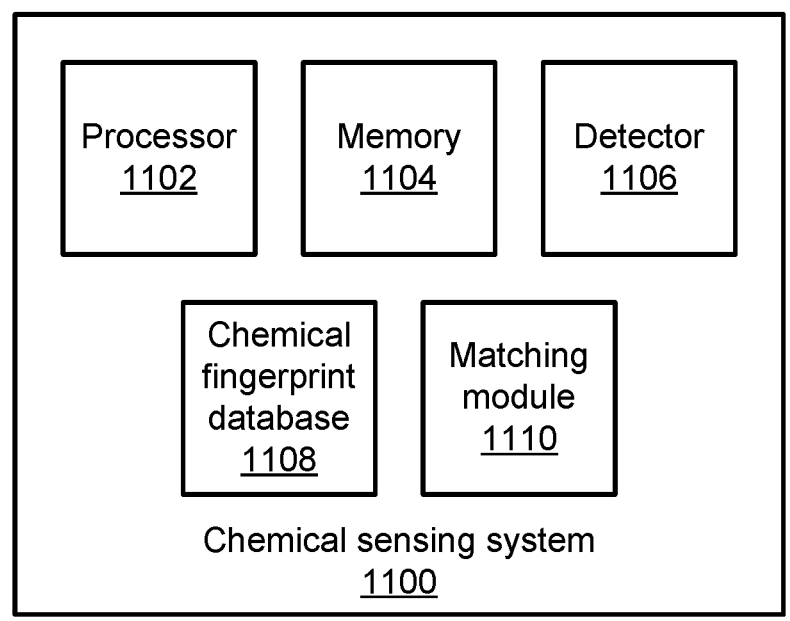
FIG. 11 is a block diagram of a chemical sensing system in accordance with the present embodiments.

Referring now to FIG. 11, a chemical sensing system 1100 is shown. It is specifically contemplated that the chemical sensing system includes the detection and analysis components of FIGS. 1 and/or 7, but it should be understood that the chemical sensing system 1100 may further include the test surfaces and light sources. The chemical sensing system 1100 includes a hardware processor 1102 and memory 1104. A detector 1106 receives a signal form a surface plasmon resonance test surface 102 or 702. Depending on the embodiment, the detector 1106 may be a light sensor that receives reflected light from test surface 102 or, alternatively, the detector 1106 may be a photothermoelectric detector that measures photothermoelectric currents generated by a test surface 702.

The chemical sensing system 1100 may furthermore include one or more functional modules that are implemented as, e.g., software that is stored in memory 1104 and executed by hardware processor 1102. Alternatively, the functional module(s) may be implemented as one or more discrete hardware components in the form of, e.g., application specific integrated chips or field programmable gate arrays.

In particular, the chemical sensing system 1100 may include a matching module 1110 that compares the signal received by the detector 1106 to one or more chemical or molecular fingerprints in a chemical fingerprint database 1108 that is stored in memory. Based on this comparison, the matching module 1110 determines a difference between the received signal and the fingerprint of a molecule in question or with all of the fingerprints in the database 1108. If the difference is within a threshold, the matching module 1110 determines that the molecule or chemical has been detected.

Figure 12:
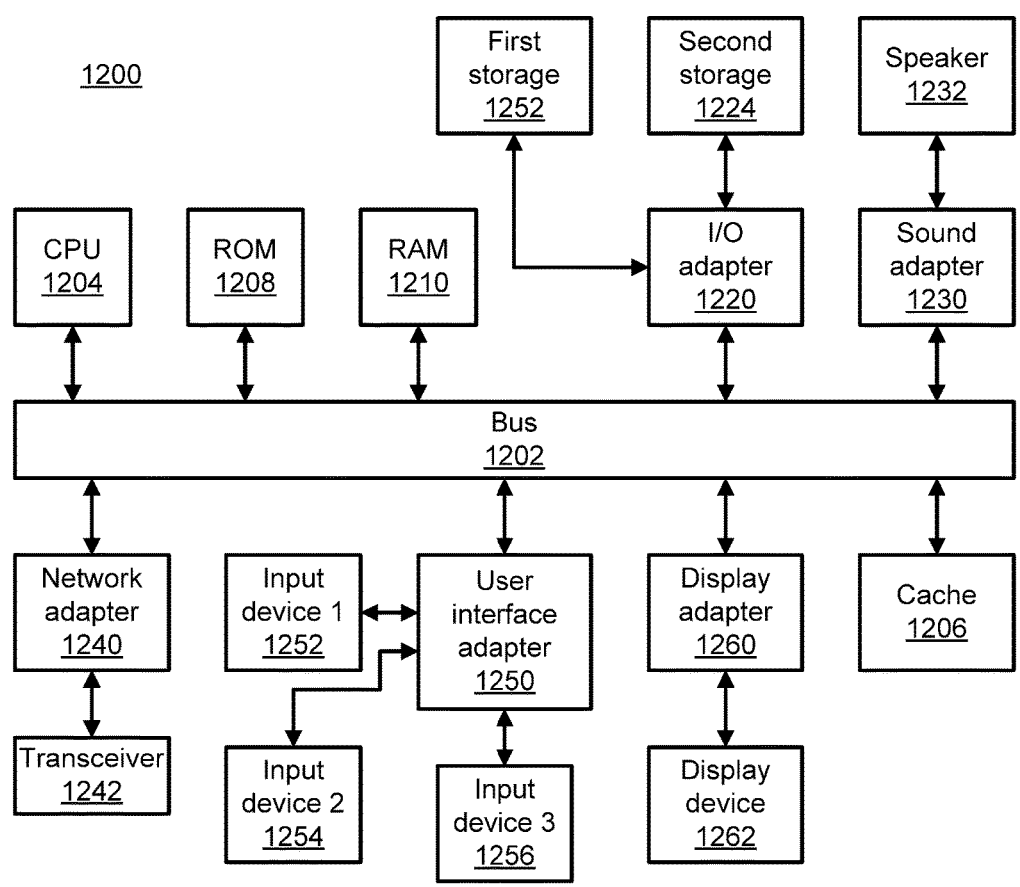
FIG. 12 is a block diagram of a processing system in accordance with the present embodiments.

Referring now to FIG. 12, an exemplary processing system 1200 is shown which may represent the transmitting device 100 or the receiving device 120. The processing system 1200 includes at least one processor (CPU) 1204 operatively coupled to other components via a system bus 1202. A cache 1206, a Read Only Memory (ROM) 1208, a Random Access Memory (RAM) 1210, an input/output (I/O) adapter 1220, a sound adapter 1230, a network adapter 1240, a user interface adapter 1250, and a display adapter 1260, are operatively coupled to the system bus 1202.

A first storage device 1222 and a second storage device 1224 are operatively coupled to system bus 1202 by the I/O adapter 1220. The storage devices 1222 and 1224 can be any of a disk storage device (e.g., a magnetic or optical disk storage device), a solid state magnetic device, and so forth. The storage devices 1222 and 1224 can be the same type of storage device or different types of storage devices.

A speaker 1232 is operatively coupled to system bus 1202 by the sound adapter 1230. A transceiver 1242 is operatively coupled to system bus 1202 by network adapter 1240. A display device 1262 is operatively coupled to system bus 1202 by display adapter 1260.

A first user input device 1252, a second user input device 1254, and a third user input device 1256 are operatively coupled to system bus 1202 by user interface adapter 1250. The user input devices 1252, 1254, and 1256 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles.

The user input devices 1252, 1254, and 1256 can be the same type of user input device or different types of user input devices. The user input devices 1252, 1254, and 1256 are used to input and output information to and from system 1200.

Of course, the processing system 1200 may also include other elements (not shown), as readily contemplated by one of skill in the art, as well as omit certain elements. For example, various other input devices and/or output devices can be included in processing system 1200, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 1200 are readily contemplated by one of ordinary skill in the art given the teachings of the present principles provided herein.

Having described preferred embodiments of chemical sensing based on plasmon resonance in carbon nanotubes (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A chemical sensor, comprising:
   a carbon nanotube test surface;
   a detector configured to receive a signal from the carbon nanotube test surface responsive to illumination on the nanotube test surface; and
   a matching module configured to determine whether a chemical is present at the carbon nanotube test surface based on a comparison between the signal and a spectral profile of the chemical that is based on an overlap between plasmon modes and vibrational modes of the chemical and the detector.

2. The chemical sensor of claim 1, wherein the nanotube test surface comprises strips of carbon nanotube film.

3. The chemical sensor of claim 2, wherein the nanotube test surface further comprises conductive contacts at respective ends of the strips of carbon nanotube film.

4. The chemical sensor of claim 3, wherein the detector is a photothermoelectric detector configured to receive a photothermoelectric signal from the carbon nanotube test surface.

5. The chemical sensor of claim 2, wherein the strips of carbon nanotube film have equal widths and are disposed at regular intervals on a dielectric surface.

6. The chemical sensor of claim 5, wherein the carbon nanotube test surface further comprises an electrode positioned under the dielectric surface.

7. The chemical sensor of claim 6, wherein the electrode is configured to apply a voltage to the detector that tunes a plasmon resonance frequency of the detector.

8. The chemical sensor of claim 1, wherein the detector is a photodetector configured to receive light reflected from the carbon nanotube test surface.

9. A method of chemical sensing, comprising:
   illuminating a carbon nanotube test surface;
   detecting a signal from the carbon nanotube test surface responsive to the illumination of the carbon nanotube test surface; and
   determining whether the chemical is present at the carbon nanotube test surface based on a comparison between the signal and a spectral profile of the chemical that is based on an overlap between plasmon modes and vibrational modes of the chemical and the detector.

10. The method of claim 9, wherein the nanotube test surface comprises strips of carbon nanotube film.

11. The method of claim 10, wherein the nanotube test surface further comprises conductive contacts at respective ends of the strips of carbon nanotube film.

12. The method of claim 11, wherein detecting the signal comprises receiving a photothermoelectric current from the carbon nanotube test surface.

13. The method of claim 10, wherein the strips of carbon nanotube film have equal widths and are disposed at regular intervals on a dielectric surface.

14. The method of claim 13, wherein the carbon nanotube test surface further comprises an electrode positioned under the dielectric surface.

15. The method of claim 14, further comprising adjusting a voltage on the electrode to tune a spectral sensitivity of the carbon nanotube test surface.

16. The method of claim 10, detecting the signal comprises receiving light reflected from the carbon nanotube test surface.

17. The method of claim 9, further comprising applying a voltage to an electrode under the detector to tune a plasmon resonance frequency of the detector.

* * * * *